US007183060B2

(12) United States Patent
O'Connor, Jr.

(10) Patent No.: US 7,183,060 B2
(45) Date of Patent: Feb. 27, 2007

(54) **PEPTIDES FOR DETECTION OF ANTIBODY TO *EHRLICHIA EWINGII***

(75) Inventor: Thomas Patrick O'Connor, Jr., Westbrook, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 135 days.

(21) Appl. No.: 11/063,027

(22) Filed: Feb. 22, 2005

(65) Prior Publication Data

US 2006/0189537 A1   Aug. 24, 2006

(51) Int. Cl.
*G01N 33/569* (2006.01)
*C07K 7/08* (2006.01)

(52) U.S. Cl. .................. 435/7.1; 530/326; 530/350
(58) Field of Classification Search ................. None
See application file for complete search history.

(56) References Cited

U.S. PATENT DOCUMENTS

| | | | |
|---|---|---|---|
| 5,192,679 | A | 3/1993 | Dawson et al. |
| 5,401,656 | A | 3/1995 | Dawson |
| 5,413,931 | A | 5/1995 | Dawson et al. |
| 5,726,010 | A | 3/1998 | Clark |
| 5,789,176 | A | 8/1998 | Dawson et al. |
| 5,869,335 | A | 2/1999 | Munderloh et al. |
| 5,928,879 | A | 7/1999 | Dumler et al. |
| 5,955,359 | A | 9/1999 | Dumler et al. |
| 5,976,791 | A | 11/1999 | Mabilat et al. |
| 5,976,860 | A | 11/1999 | Coughlin et al. |
| 5,989,848 | A | 11/1999 | Dawson |
| 6,015,691 | A | 1/2000 | Walker et al. |
| 6,025,338 | A | 2/2000 | Barbet et al. |
| 6,034,085 | A | 3/2000 | Joshi et al. |
| 6,204,252 | B1 | 3/2001 | Murphy et al. |
| 6,207,169 | B1 | 3/2001 | Reed et al. |
| 6,231,869 | B1 | 5/2001 | Reed et al. |
| 6,251,872 | B1 | 6/2001 | Barbet et al. |
| 6,277,381 | B1 | 8/2001 | Reed et al. |
| 6,284,238 | B1 | 9/2001 | Coughlin et al. |
| 6,306,394 | B1 | 10/2001 | Murphy et al. |
| 6,306,402 | B1 | 10/2001 | Reed et al. |
| 6,355,777 | B1 | 3/2002 | Walker et al. |
| 6,392,023 | B1 | 5/2002 | Walker et al. |
| 6,403,780 | B1 | 6/2002 | Walker et al. |
| 6,458,942 | B1 | 10/2002 | Walker et al. |
| 6,593,147 | B1 | 7/2003 | Barbet et al. |
| 2002/0064531 | A1 | 5/2002 | Walker et al. |
| 2002/0064535 | A1 | 5/2002 | Reed et al. |
| 2002/0068343 | A1 | 6/2002 | Reed et al. |
| 2002/0086984 | A1 | 7/2002 | Reed et al. |
| 2002/0115840 | A1 | 8/2002 | Walker et al. |
| 2002/0132789 | A1 | 9/2002 | Barbet et al. |
| 2002/0177178 | A1 | 11/2002 | Lawton et al. |
| 2003/0129680 | A1 | 7/2003 | O'Connor |

FOREIGN PATENT DOCUMENTS

| WO | 9913720 | 3/1999 |
|---|---|---|
| WO | WO 02/057794 | 7/2002 |

OTHER PUBLICATIONS

Ohashi, et al., "Immunodominant Major Outer Membrane Proteins of *Ehrlichia chaffeensis* are Encoded by a Polymorphic Multigene Family", *Infection and Immunity*, p. 132-139, vol. 66, No. 1, 1998.
Ohashi, et al., "Cloning and Characterization of Multigenes Encoding the Immunodominant 30-Kilodalton Major Outer Membrane Proteins of *Ehrlichia canis* and Application of the Recombinant Protein for Serodiagnosis", *Journal of Clinical Microbiology*, p. 2671-2680, vol. 36, No. 9, Sep. 1998.
Yu, et al., "Genetic Diversity of the 28-Kilodalton Outer Membrane Protein Gene in Human Isolates of *Ehrlichia chaffeensis*", *Journal of Clinical Microbiology*, p. 1137-1143, vol. 37, No. 4, Apr. 1999.
McBride, et al., "Molecular Cloning of the Gene for a Conserved Major Immunoreactive 28-Kilodalton Protein of *Ehrlichia canis*: a Potential Serodiagnostic Antigen", *Clinical and Diagnostic Laboratory Immunology*, p. 392-399, vol. 6, No. 3, May 1999.
Yu, et al., "Comparison of *Ehrlichia chaffeensis* Recombinant Proteins for Serologic Diagnosis of Human *Monocytotropic Ehrlichiosis*", *Journal of Clinical Microbiology*, p. 2568-2575, vol. 37, No. 8, Aug. 1999.
Yu, et al., "Characterization of the complete transcriptionally active *Ehrlichia chaffeensis* 28 kDa outer membrane protein multigene family", *Gene* 248, p. 59-68, Dec. 1999.
McBride, et al., "A conserved, transcriptionally active p28 multigene locus of *Ehrlichia canis*", *Gene* 254, p. 245-252, Feb. 2000.
Suksawat, et al., "Seroprevalence of *Ehrlichia canis*, *Ehrlichia equi*, and *Ehrlichia ristricii* in Sick Dogs from North Carolina and Virginia", *J. Vet. Interm. Med.*, 14:50-55, 2000.
Waner, et al., "Comparison of clinic-based ELISA test kit with the immunofluorescence test for the assay of *Ehrlichia canis* antibodies in dogs", *J. Vet. Diagn. Invest.*, vol. 12, pp. 240-244, 2000.
Cadman, et al., "Comparison of the dot-blot enzyme linked immunoassay with immunofluorescence for detecting antibodies to *Ehrlichia canis*", *The Veterinary Record*, 135, 362, 1994.
Zhi, et al., "Cloning and Expression of the 44-Kilodalton Major Outer Membrane Protein Gene of the Human *Granulocytic Ehrlichiosis* Agent and Application of the Recombinant Protein to Serodiagnosis", *Journal of Clinical Microbiology*, vol. 36, No. 6, pp. 1666-1673, 1998.
McBride, et al., "Immunodiagnosis of *Ehrlichia canis* Infection with Recombinant Proteins", *Journal of Clinical Microbiology*, vol. 39, No. 1, pp. 315-322, 2001.
Unver, et al., "Western and Dot Blotting Analyses of *Ehrlichia chaffeensis* indirect Fluorescent-Antibody Assay-Positive and -Negative Human Sera by Using Native and Recombinant *E. chaffeensis* and *E. canis* Antigens", *Journal of Clinical Microbiology*, vol. 37, No. 12, pp. 3888-3895, 1999.
Gusa, et al., *Journal of Clinical Microbiology*, vol. 39, No. 11, pp. 3871-3876 (2001).

(Continued)

*Primary Examiner*—Robert A. Wax
(74) *Attorney, Agent, or Firm*—McDonnell Boehnen Hulbert & Berghoff LLP

(57) ABSTRACT

The invention provides compositions and methods for the detection and quantification of *Ehrlichia ewingii*, *Ehrlichia ewingii* antibodies, antibody fragments, and polypeptides.

28 Claims, No Drawings

OTHER PUBLICATIONS

Knowles, et al., "Characterization of the Major Antigenic Protein 2 of *Ehrlichia canis* and *Ehrlichia chaffeensis* and its Application for Serodiagnosis of *Ehrlichiosis*", Clinical and Diagnostic Laboratory Immunology, vol. 10, No. 4, p. 520-524 (2003).

AX548673, Database EPO Proteins dated Nov. 26, 2002 "SEQ 2 from WO 02/057794".

Database gene sequence dated Jan. 15, 2004, "*Ehrlichia canis* detection associate peptide SEQ ID No. 3" ADD40755.

International Search Report dated Oct. 4, 2006 for corresponding PCT application PCT/US2006/005084.

PEPTIDES FOR DETECTION OF ANTIBODY TO *EHRLICHIA EWINGII*

FIELD OF THE INVENTION

The invention relates to methods and compositions for the detection and quantification of *Ehrlichia ewingii* antibodies and antibody fragments, *E. ewingii*, and *E. ewingii* polypeptides.

BACKGROUND OF THE INVENTION

Granulocytic ehrlichiosis occurs in mammals and is caused by infection of granulocytic cells with the tick-borne agent *E. ewingii*. Frequently reported symptoms of granulocytic ehrlichiosis in humans are anemia and thrombocytopenia. Common clinical signs in dogs are fever and lameness.

Indirect immunofluorescence assays (IFA) and enzyme-linked immunosorbent assays (ELISA) are frequently used as aids in the diagnosis of diseases caused by *E. ewingii* by measuring the binding of antibody from a patient's blood or serum to infected cells, cell lysates or purified Ehrlichial proteins. Commonly, these tests are made using Ehrlichia species other than *E. ewingii* (for example *E. canis* or *E. chaffeensis*) as surrogate markers because *E. ewingii*-specific reagents are not easily grown in tissue culture and, therefore, have heretofore been unavailable for, e.g., Immuno-Fluorescence Assays (IFA). Assays using surrogate markers are severely limited in usefulness because of sensitivity and specificity issues directly related to the impure nature and the non-specific nature of the antigen or antigens used in these tests. Highly purified reagents are needed to construct more accurate assays. This invention discloses specific synthetic peptide sequences derived from *E. ewingii* that can be used in place of purified proteins, partially purified proteins, infected cells, or cell lysates from Ehrlichia species other than *E. ewingii*.

SUMMARY OF THE INVENTION

One embodiment of the invention provides a composition of matter comprising a purified polypeptide consisting essentially of SEQ ID NO:3 or SEQ ID NO:4. The purified polypeptide can consist essentially of SEQ ID NO: 1 or SEQ ID NO:2. The purified polypeptide can consist essentially of SEQ ID NO: 1, SEQ ID NO:2, SEQ ID NO:3, SEQ ID NO:4 or a combination thereof. The purified polypeptide can be in a multimeric form and can further comprise a carrier. The purified polypeptide can be linked to an indicator reagent, an amino acid spacer, an amino acid linker, a signal sequence, a stop transfer sequence, a transmembrane domain, a protein purification ligand, or a combination thereof.

Another embodiment of the invention provides a purified fusion polypeptide comprising polypeptides of SEQ ID NO:1, SEQ ID NO:2, SEQ ID NO:3, SEQ ID NO:4 or a combination thereof. At least one of the polypeptides can be in a multimeric form. The purified fusion polypeptide can be linked to an indicator reagent, an amino acid spacer, an amino acid linker, a signal sequence, a stop transfer sequence, a transmembrane domain, a protein purification ligand or a combination thereof.

Even another embodiment of the invention provides a purified polynucleotide encoding a purified polypeptide or purified fusion protein of the invention.

Still another embodiment of the invention provides a method of detecting antibodies that specifically bind *E. ewingii* or an *E. ewingii* polypeptide. The method can comprise contacting a purified polypeptide comprising SEQ ID NO:1, SEQ ID NO:2, SEQ ID NO:3, SEQ ID NO:4, or a combination thereof, with a test sample suspected of comprising antibodies specific for *E. ewingii*, under conditions that allow polypeptide/antibody complexes to form and detecting polypeptide/antibody complexes. The detection of polypeptide/antibody complexes is an indication that antibodies specific for *E. ewingii* are present in the test sample, and the absence of polypeptide/antibody complexes is an indication that antibodies specific for *E. ewingii* are not present in the test sample. The antibodies can be fragments of antibodies. The amount of antibody in the test sample can be determined. The polypeptide can be attached to a substrate. The polypeptide can be attached to an indicator reagent. The polypeptide/antibody complexes can be detected using a labeled anti-species antibody. The test sample can comprise a biological sample obtained from a mammal. The mammal can be selected from the group consisting of humans, cats, horses, and dogs. The method can comprise an assay selected from the group of assays consisting of a microtiter plate assay, a reversible flow chromatographic binding assay, an enzyme linked immunosorbent assay, a radioimmunoassay, a hemagglutination assay a western blot assay, a fluorescence polarization immunoassay, and an indirect immunofluorescence assay.

Yet another embodiment of the invention provides a method of detecting an *E. ewingii* infection in a mammal. The method comprises obtaining a biological sample from a mammal suspected of having an *E. ewingii* infection; contacting a purified polypeptide comprising SEQ ID NO:1, SEQ ID NO:2, SEQ ID NO:3, SEQ ID NO:4, or a combination thereof with the biological sample under conditions that allow polypeptide/antibody complexes to form; and detecting polypeptide/antibody complexes. The detection of polypeptide/antibody complexes is an indication that the mammal has an *E. ewingii* infection and the absence of polypeptide/antibody complexes is an indication that the mammal does not have an *E. ewingii* infection.

Another embodiment of the invention provides an antibody that specifically binds to at least one epitope of an *E. ewingii* polypeptide, wherein said polypeptide is SEQ ID NO:1, SEQ ID NO:2, SEQ ID NO:3, or SEQ ID NO:4. The antibody can be a monoclonal antibody, polyclonal antibody or antibody fragment.

Still another embodiment of the invention provides a method of detecting an *E. ewingii* polypeptide or *E. ewingii* in a sample. The method comprises contacting one or more antibodies that specifically bind to at least one epitope of an *E. ewingii* polypeptide, wherein said polypeptide comprises SEQ ID NO:1, SEQ ID NO:2, SEQ ID NO:3, or SEQ ID NO:4 with the sample under conditions that allow polypeptide/antibody complexes to form and detecting polypeptide/antibody complexes. The detection of polypeptide/antibody complexes is an indication that *E. ewingii* or an *E. ewingii* polypeptide is present in the sample and the absence of polypeptide/antibody complexes is an indication that *E. ewingii* or an *E. ewingii* polypeptide is not present in the sample. The sample can be serum, whole blood, urine, or saliva.

The invention therefore provides methods and compositions that can be used to detect *E. ewingii* antibodies and antibody fragments, *E. ewingii*, and *E. ewingii* polypeptides with sensitivity and specificity.

DETAILED DESCRIPTION OF THE INVENTION

Immunodominant regions of a P30 protein of *E. canis* have previously been identified using phage display technology. See U.S. patent application Ser. No. 09/765,736 filed Jan. 18, 2001. The identified sequences exhibited strong homology to sequences for outer membrane proteins of several isolates of *Ehrlichia canis*. Synthetic peptides corresponding to sequences from homologous regions of several outer membrane proteins have been synthesized and used successfully in diagnostic assays to detect antibodies and antibody fragments to *E. canis*.

*E. ewingii* and *E. canis* are different species of related organisms that are classified within the same serotype of the *Ehrlichia* group. Polypeptide sequences of *E. ewingii* were examined to identify immunodominant regions. *E. ewingii* membrane proteins include C-1, OK-2, OK-1, MO-3 and MO-1 (Gusa et al., Journal of Clinical Microbiology, Vol. 39, No. 11, pp. 3871–3876 (2001)). The immunodominant *E. ewingii* peptides of the present invention were identified by comparison to *E. canis* immunodominant polypeptides. The following sequence, which corresponds to amino acid numbers 16 to 35 of an *E. ewingii* membrane protein, was identified and used as a basis to synthesize a synthetic peptide:

Peptide I. Amino Acid Nos. 16 to 35 of proteins C-1, OK-2, OK-1 and MO-3

```
AETKKTFGLEKNYDGAKIED       (SEQ ID NO:1)
```

The following sequence from a homologous gene was also identified:

Peptide II. Amino Acids Nos. 16 to 35 of protein MO-1

```
AETKRTFGLDKNYDGAQITD       (SEQ ID NO:2)
```

Another embodiment of the invention provides the following polypeptide:

Peptide III.

```
AETKXTFGLXKNYDGAXIXD,      (SEQ ID NO:3)
``` wherein X stands for any amino acid. In one embodiment of the invention, the X in position 5 of SEQ ID NO:3 can be K or R. In another embodiment of the invention, the X in position 10 of SEQ ID NO:3 can be E or D. In yet another embodiment of the invention, the X in position 17 can be K or Q. In still another embodiment of the invention, the X in position 19 can be E or T.

Another embodiment of the invention provides the following polypeptide:

Peptide IV.

```
XAETKXTFGLXKNYDGAXIXD,     (SEQ ID NO:4)
``` wherein X stands for any amino acid. In one embodiment the X in position 1 of SEQ ID NO:4 is C. In one embodiment of the invention, the X in position 6 of SEQ ID NO:4 can be K or R. In another embodiment of the invention, the X in position 111 of SEQ ID NO:4 can be E or D. In yet another embodiment of the invention, the X in position 18 of SEQ ID NO:4 can be K or Q. In still another embodiment of the invention, the X in position 20 of SEQ ID NO:4 can be E or T.

*E. ewingii* Polypeptides

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

Purified polypeptides of the invention can either be full-length polypeptides or fragments of polypeptides. For example, fragments of polypeptides of the invention can comprise about 5, 6, 7, 8, 9, 10, 11, 12, 13, 14, 15, 16, 17, 18, or 19 amino acids of polypeptides of the invention. Examples of polypeptides of the invention include those shown in SEQ ID NOs:1, 2, 3 and 4. Variant polypeptides are at least about 80, or about 90, 96, 98, or 99% identical to the polypeptide sequences shown in SEQ ID NOs:1–4 and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing. Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482–489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90–110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide. Variant polypeptides of the invention can comprise about 1, 2, 3, 4, 5, or 6 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. More than one polypeptide of the invention can be present in a fusion protein. Fragments of polypeptides of the invention can be present in a fusion protein. A fusion protein of the invention can comprise one or more of SEQ ID NO:1, SEQ ID NO:2, SEQ ID NO:3, SEQ ID NO:4, fragments thereof, or combinations thereof.

Polypeptides of the invention can be in a multimeric form. That is, a polypeptide can comprise one or more copies of SEQ ID NOs:1–4 or a combination thereof. A multimeric polypeptide can be a multiple antigen peptide (MAP). See e.g., Tam, J. Immunol. Methods, 196:17–32 (1996).

Polypeptides of the invention can comprise an antigen that is recognized by an antibody reactive against *E. ewingii*. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181–186 (1988). For example, a polypeptide of the invention can be isolated and screened. A series of short peptides, which together span an entire polypeptide sequence, can be prepared by proteolytic cleavage. By starting with, for example, 20-mer polypeptide fragments, each fragment can be tested for the presence of epitopes recognized in an ELISA. For example, in an ELISA assay an *E. ewingii* polypeptide, such as a 20-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 20-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *E. ewingii* cells.

An immunogenic polypeptide of the invention can comprise an amino acid sequence shown in SEQ ID NOs:1–4. An immunogenic polypeptide can elicit antibodies or other immune responses (e.g., T-cell responses of the immune system) that recognize epitopes of polypeptides having SEQ ID NOs:1–4. An immunogenic polypeptide of the invention can also be a fragment of a polypeptide that has an amino acid sequence shown in SEQ ID NOs:1–4. An immunogenic polypeptide fragment of the invention can be about 5, 6, 7, 8, 9, 10, 11, 12, 13, 14, 15, 16, 17, 18, 19, or 20 amino acids in length.

*E. ewingii* Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides of the invention encode the polypeptides described above. In one embodiment of the invention the polynucleotides encode polypeptides shown in SEQ ID NOs:1–4 or combinations thereof. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of *E. ewingii* polynucleotides that encode biologically functional *E. ewingii* polypeptides also are *E. ewingii* polynucleotides. Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC 1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Polynucleotides of the invention can be used, for example, as probes or primers, for example PCR primers, to detect the presence of *E. ewingii* polynucleotides in a sample, such as a biological sample. The ability of such probes and primers to specifically hybridize to *E. ewingii* polynucleotide sequences will enable them to be of use in detecting the presence of complementary sequences in a given sample. Polynucleotide probes and primers of the invention can hybridize to complementary sequences in a sample such as a biological sample, including saliva, sputum, blood, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9 M salt, at temperatures ranging from about 20° C. to about 55° C. The presence of a hybridized complex comprising the probe or primer and a complementary polynucleotide from the test sample indicates the presence of *E. ewingii* or an *E. ewingii* polynucleotide sequence in the sample.

Antibodies

Antibodies of the invention are antibody molecules that specifically and stably bind to an *E. ewingii* polypeptide of the invention or fragment thereof. An antibody of the invention can be a polyclonal antibody, a monoclonal antibody, a single chain antibody (scFv), or a fragment of an antibody. Fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23–37 (1998); Dean, *Methods Mol.*

Biol. 32:361–79 (1994); Baileg, *Methods Mol. Biol.* 32:381–88 (1994); Gullick, *Methods Mol. Biol.* 32:389–99 (1994); Drenckhahn et al. *Methods Cell. Biol.* 37:7–56 (1993); Morrison, *Ann. Rev. Immunol.* 10:239–65 (1992); Wright et al. *Crit. Rev. Immunol.* 12:125–68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that the polypeptide recognizes and binds to an antibody of the invention with greater affinity than to other, non-specific molecules. For example, an antibody raised against an antigen (e.g., a polypeptide) to which it binds more efficiently than to a non-specific protein can be described as specifically binding to the antigen. Binding specifically can be tested using, for example, an enzyme-linked immunosorbant assay (ELISA), a radioimmunoassay (RIA), or a western blot assay using methodology well known in the art.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing *E. ewingii*-specific antibodies can be identified using RIA or ELISA and isolated by cloning in semi-solid agar or by limiting dilution. Clones producing *E. ewingii*-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. Nos. 4,474,893; 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), or human antibodies. Human antibodies can be made by, for example, direct immortilization, phage display, transgenic mice, or a Trimera methodology, see e.g., Reisener et al., *Trends Biotechnol.* 16:242–246 (1998).

Antibodies that specifically bind *E. ewingii* antigens (e.g., *E. ewingii* polypeptides), are particularly useful for detecting the presence of *E. ewingii* or *E. ewingii* antigens in a sample, such as a serum, blood, urine or saliva sample from an *E. ewingii*-infected animal such as a human. An immunoassay for *E. ewingii* or an *E. ewingii* antigen can utilize one antibody or several antibodies. An immunoassay for *E. ewingii* or an *E. ewingii* antigen can use, for example, a monoclonal antibody directed towards an *E. ewingii* epitope, a combination of monoclonal antibodies directed towards epitopes of one *E. ewingii* polypeptide, monoclonal antibodies directed towards epitopes of different *E. ewingii* polypeptides, polyclonal antibodies directed towards the same *E. ewingii* antigen, polyclonal antibodies directed towards different *E. ewingii* antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of *E. ewingii* or a *E. ewingii* antigen. Supports include, for example, glass, polystyrene, polypropylene, polyethylene, dextran, nylon, amylases, natural and modified celluloses, polyacrylamides, agaroses and magletite.

Antibodies of the invention can further be used to isolate *E. ewingii* organisms or *E. ewingii* antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind *E. ewingii* organisms or *E. ewingii* antigens from a sample, such as a biological sample including saliva, serum, sputum, blood, urine, feces, cerebrospinal fluid, amniotic fluid, wound exudate, or tissue. The bound *E. ewingii* organisms or *E. ewingii* antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by *E. ewingii*. By measuring the increase or decrease of *E. ewingii* antibodies to *E. ewingii* antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Methods of Detection

The methods of the invention can be used to detect antibodies or antibody fragments specific for *E. ewingii* in a test sample, such as a biological sample, an environmental sample, or a laboratory sample. A biological sample can include, for example, sera, blood, cells, plasma, or tissue from a mammal such as a horse, cat, dog or human. The test sample can be untreated, precipitated, fractionated, separated, diluted, concentrated, or purified before combining with a polypeptide of the invention.

The methods comprise contacting a polypeptide of the invention with a test sample under conditions that allow a polypeptide/antibody complex, i.e., an immunocomplex, to form. That is, a polypeptide of the invention specifically binds to an antibody specific for *E. ewingii* located in the sample. One of skill in the art is familiar with assays and conditions that are used to detect antibody/polypeptide complex binding. The formation of a complex between polypeptides and anti-*E. ewingii* antibodies in the sample is detected.

An antibody of the invention can be used in a method of the diagnosis of *E. ewingii* infection by obtaining a test sample from a human or animal suspected of having an *E. ewingii* infection. The test sample is contacted with an antibody of the invention under conditions enabling the formation of an antibody-antigen complex (i.e., an immunocomplex). The amount of antibody-antigen complexes can be determined by methodology known in the art. A level that is higher than that formed in a control sample indicates an *E. ewingii* infection. Alternatively, a polypeptide of the invention can be contacted with a test sample. *E. ewingii* antibodies in a positive body sample will form an antigen-antibody complex under suitable conditions. The amount of antibody-antigen complexes can be determined by methods known in the art.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, antibodies of the invention are attached to a solid phase or substrate. A test sample potentially comprising a protein comprising a polypeptide of the invention is added to the substrate. Antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, antibodies of the invention are attached to a solid phase or substrate. A test sample potentially comprising a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise and indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay of the invention comprises a reversible flow chromatographic binding assay, for example a SNAP® assay. See U.S. Pat. No. 5,726,010.

Assays can use solid phases or substrates or can be performed by immunoprecipitation or any other methods that do not utilize solid phases. Where a solid phase or substrate is used, a polypeptide of the invention is directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). A preferred substrate is sintered, fine particles of polyethylene, commonly known as porous polyethylene, for example, 10–15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one type of assay format, one or more polypeptides can be coated on a solid phase or substrate. A test sample suspected of containing an anti-*E. ewingii* antibody or fragment thereof is incubated with an indicator reagent comprising a signal generating compound conjugated to an antibody or antibody fragment specific for *E. ewingii* for a time and under conditions sufficient to form antigen/antibody complexes of either antibodies of the test sample to the polypeptides of the solid phase or the indicator reagent compound conjugated to an antibody specific for *E. ewingii* to the polypeptides of the solid phase. The reduction in binding of the indicator reagent conjugated to an anti-*E. ewingii* antibody to the solid phase can be quantitatively measured. A measurable reduction in the signal compared to the signal generated from a confirmed negative *E. ewingii* test sample indicates the presence of anti-*E. ewingii* antibody in the test sample. This type of assay can quantitate the amount of anti-*E. ewingii* antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If *E. ewingii* antibodies are present in the test sample they will bind the polypeptide conjugated to an indicator reagent and to the polypeptide immobilized on the support. The polypeptide/antibody/indicator complex can then be detected. This type of assay can quantitate the amount of anti-*E. ewingii* antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If *E. ewingii* antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-*E. ewingii* antibodies in a test sample.

The formation of a polypeptide/antibody complex or a polypeptide/antibody/indicator complex can be detected by radiometric, colormetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-*E. ewingii* antibodies in a test sample. Therefore, the methods of the invention can be used to diagnose *E. ewingii* infection in a patient.

The methods of the invention can also indicate the amount or quantity of anti-*E. ewingii* antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrate specimens such as urine, in order to determine the presence and/or amount of antibody present.

The invention further comprises assay kits (e.g., articles of manufacture) for detecting anti-*E. ewingii* antibodies or antibody fragments, *E. ewingii*, or *E. ewingii* polypeptides in a sample. A kit comprises one or more polypeptides of the invention and means for determining binding of the polypeptide to anti-*E. ewingii* antibodies or antibody fragments in the sample. A kit or article of manufacture can also comprise one or more antibodies or antibody fragments of the invention and means for determining binding of the antibodies or antibody fragments to *E. ewingii* or *E. ewingii* polypeptides in the sample. A kit can comprise a device containing one or more polypeptides or antibodies of the invention and instructions for use of the one or more polypeptides or antibodies for, e.g., the identification of an *E. ewingii* infection in a mammal. The kit can also comprise packaging material comprising a label that indicates that the one or more polypeptides or antibodies of the kit can be used for the identification of *E. ewingii* infection. Other components such as buffers, controls, and the like, known to those of ordinary skill in art, can be included in such test kits. The polypeptides, antibodies, assays, and kits of the invention are useful, for example, in the diagnosis of individual cases of *E. ewingii* infection in a patient, as well as epidemiological studies of *E. ewingii* outbreaks.

Polypeptides and assays of the invention can be combined with other polypeptides or assays to detect the presence of *E. ewingii* along with other organisms. For example, polypeptides and assays of the invention can be combined with reagents that detect heartworm and/or *Borrelia burgdorferi* and/or *Anaplasma phagocytophila* and/or *Ehrlichia canis*.

Methods of Treatment, Amelioration, or Prevention of a Disease Caused by *E. ewingii*

Polypeptides, polynucleotides, and antibodies of the invention can be used to treat, ameliorate, or prevent a disease caused by *E. ewingii*. For example, an antibody, such as a monoclonal antibody of the invention or fragments thereof, can be administered to an animal, such as a human. In one embodiment of the invention an antibody or fragment thereof is administered to an animal in a pharmaceutical composition comprising a pharmaceutically acceptable carrier. A pharmaceutical composition comprises a therapeutically effective amount of an antibody or fragments thereof. A therapeutically effective amount is an amount effective in alleviating the symptoms of *E. ewingii* infection or in reducing the amount of *E. ewingii* organisms in a subject.

Polypeptides or polynucleotides of the invention can be present in an immunogenic composition and used to elicit an immune response in a host. An immunogenic composition is capable of inducing an immune response in an animal. An immunogenic polypeptide or polynucleotide composition of the invention is particularly useful in sensitizing an immune system of an animal such that, as one result, an immune response is produced that ameliorates or prevents the effect of *E. ewingii* infection. The elicitation of an immune response in animal model can be useful to determine, for example, optimal doses or administration routes. Elicitation of an immune response can also be used to treat, prevent, or ameliorate a disease or infection caused by *E. ewingii*. An immune response includes humoral immune responses or cell mediated immune responses, or a combination thereof. An immune response can also comprise the promotion of a generalized host response, e.g., by promoting the production of defensins.

The generation of an antibody titer by an animal against *E. ewingii* can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to *E. ewingii* can be identified by eliciting antibodies directed against *E. ewingii* polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptides, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $Alk(SO_4)_2$; $AlNa(SO_4)_2$, $AlNH_4(SO_4)$, Silica, Alum, $Al(OH)_3$, and $Ca_3(PO_4)_2$), polynucleotides (i.e. Polyic and Poly AU acids), and certain natural substances (e.g. wax D from *Mycobacterium tuberculosis*, as well as substances found in *Corynebacterium parvum, Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® 80 emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a mammal, such as a baboon, chimpanzee, dog, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a mammal at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with *E. ewingii* or can be administered to an *E. ewingii*-infected animal. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above. All references cited in this disclosure are incorporated herein by reference.

EXAMPLES

Example 1

Assay Results Using Anti-species Conjugate as Indicator

Three *E. ewingii* antibody positive and three *E. ewingii* antibody negative canine samples were obtained from Sinclair Research (Columbia, Mo.). The positive and negative samples were tested for Ehrlichia antibody using an *E. canis* IFA by IDEXX Laboratory Services Reference Laboratory using *E. canis* whole cell lysate as the antigen source. Animals whose blood was reactive in the *E. canis* IFA and non-reactive for *E. canis* antibody in a species-specific serological assay for *E. canis* antibody was suspected of contracting an Ehrlichia infection other than *E. canis*. The samples were subsequently tested for antibody to *E. canis* using the licensed IDEXX SNAP® 3Dx® test and were shown to be negative for *E. canis* antibody. Assay results are shown in Table 1.

Results of the *E. ewingii*-antibody microtiter-plate based immunoassay were obtained using a synthetic peptide shown in SEQ ID NO:1 The synthetic peptide was immobilized on microtiter wells and a dilution of the test sample was added to the microtiter well and unbound antibody was removed by washing. Antibody bound to the immobilized peptide was detected by reaction with an anti-species, in this case canine, horseradish peroxidase (HRPO) conjugate, washing and addition of a HRPO substrate. The optical density of individual microtiter wells was determined using a microtiter plate reader. The results are shown in Table 1.

Example 2

Assay Results Using *E. ewingii* Synthetic Peptide (SEQ ID NO:1) Conjugate as Indicator Three *E. ewingii* antibody positive and three *E. ewingii* antibody negative canine samples were obtained from the Sinclair Research. The positive and negative samples were supplied with *E. canis* IFA titers determined by IDEXX Laboratory Services Reference Laboratory using an *E. canis* whole cell lysate as an antigen source for the IFA slide. The IFA samples were subsequently tested for antibody to *E. canis* using the licensed IDEXX SNAP® 3Dx® test and were shown to be negative for *E. canis* antibody.

Results of the *E. ewingii*-antibody microtiter-plate based immunoassay were obtained using the synthetic peptide shown in SEQ ID NO:1. The synthetic peptide was immobilized on microtiter wells and was conjugated to an indicator reagent, in this case horseradish peroxidase (HRPO). The test sample and the immunoassay peptide/indicator were added to the coated microtiter well, which was incubated and washed. Antibody bound to the immobilized peptide and the peptide/indicator reagent was immobilized in the microtiter well. This complex was detected by addition of an HRPO substrate reagent. The optical density of individual microtiter wells was determined using a microtiter plate reader. The results are shown in Table II.

TABLE I

IFA Titer Results Compared to microtiter plate-based ELISA results using *E. ewingii* peptide (SEQ ID NO: 1) coated on solid support and anti-canine/indicator for detection.

| Sample ID | IFA Titer (Result) | *E. canis* Result on SNAP 3Dx | *E. ewingii* microtiter plate, Optical Density (Result) |
|---|---|---|---|
| 20858 | <1:25 (Neg) | Neg | 0.036 (Neg) |
| 20861 | <1:25 (Neg) | Neg | 0.036 (Neg) |
| 20863 | <1:25 (Neg) | Neg | 0.034 (Neg) |
| 20972M | 1:400 (Pos) | Neg | 0.576 (Pos) |
| 20973M | 1:100 (Pos) | Neg | 0.682 (Pos) |
| 21006M | 1:100 (Pos) | Neg | 0.487 (Pos) |

TABLE II

IFA Titer Results Compared to microtiter plate-based ELISA results using *E. ewingii* peptide (SEQ ID No. 1) coated on solid support and *E. ewingii* peptide (Seq ID No. 1)/indicator for detection.

| Sample ID | IFA Titer (Result) | *E. canis* Result on SNAP 3Dx | *E. ewingii* microtiter plate, Optical Density (Result) |
|---|---|---|---|
| 20858 | <1:25 (Neg) | Neg | 0.045 (Neg) |
| 20861 | <1:25 (Neg) | Neg | 0.035 (Neg) |
| 20863 | <1:25 (Neg) | Neg | 0.043 (Neg) |
| 20972M | 1:400 (Pos) | Neg | 1.807 (Pos) |
| 20973M | 1:100 (Pos) | Neg | 1.707 (Pos) |
| 21006M | 1:100 (Pos) | Neg | 0.852 (Pos) |

What is claimed is:

1. A composition of matter comprising a purified polypeptide consisting of SEQ ID No.: 3.

2. The composition of matter of claim 1, wherein the purified polypeptide consists of SEQ ID No.: 1, SEQ ID No.: 2 or SEQ ID No.: 4.

3. The composition of matter of claim 1, wherein the purified polypeptide consists of SEQ ID No.: 1, SEQ ID No.: 2, SEQ ID No.: 3, SEQ ID No.: 4 or a combination thereof.

4. The composition of matter of claim 1, wherein the purified polypeptide is in a multimeric form.

5. The composition of matter of claim 1, further comprising a carrier.

6. The composition of matter of claim 1, wherein the purified polypeptide is linked to an indicator reagent, an amino acid spacer, an amino acid linker, a signal sequence, a stop transfer sequence, a transmembrane domain, a protein purification ligand, or a combination thereof.

7. The composition of matter of claim 1 wherein the purified polypeptide is SEQ ID No.: 4.

8. A purified fusion polypeptide comprising one or more polypeptides of SEQ ID No.: 1, SEQ ID No.: 2, SEQ ID No.: 3, SEQ ID No.: 4; wherein the one or more polypeptides are fused to an indicator reagent, an amino acid spacer, an amino acid linker, a signal sequence, a stop transfer sequence, a transmembrane domain, a protein purification ligand or a combination thereof.

9. The purified fusion polypeptide of claim 8, wherein at least one of the one or more polypeptides is in a multimeric form.

10. The purified fusion polypeptide of claim 8, wherein the wherein the one or more polypeptide are fused to an indicator reagent.

11. A method of detecting antibodies that specifically bind *Ehrlichia ewingii* or an *E. ewingii* polypeptide comprising:
   (a) contacting a purified polypeptide consisting of SEQ ID No.: 1, SEQ ID No.: 2, SEQ ID No.: 3, SEQ ID No.: 4 or a combination thereof, with a test sample suspected of comprising antibodies specific for *E. ewingii*, under conditions that allow polypeptide/antibody complexes to form;
   (b) detecting polypeptide/antibody complexes;
   wherein the detection of polypeptide/antibody complexes is an indication that antibodies specific for *E. ewingii* are present in the test sample, and wherein the absence of polypeptide/antibody complexes is an indication that antibodies specific for *E. ewingii* are not present in the test sample.

12. The method of claim 11, further comprising contacting the complexes of (a) with an indicator reagent prior to the performance of (b).

13. The method of claim 12, wherein the antibodies are fragments of antibodies, wherein the fragments of antibodies comprise Fab, Fab', Fab'-SH, F (ab')$_2$, Fv fragments or combinations thereof.

14. The method of claim 11, wherein the amount of antibody in the test sample is determined.

15. The method of claim 11, wherein the polypeptide is attached to a substrate.

16. The method of claim 11 wherein the polypeptide is attached to an indicator reagent.

17. The method of claim 16, wherein the indicator reagent comprises horseradish peroxidase.

18. The method of claim 11, wherein the polypeptide is in a multimeric form.

19. The method of claim 1, wherein the purified polypeptide is a fusion protein comprising one or more polypeptides of SEQ ID No.: 1, SEQ ID No.: 2, SEQ ID No.: 3, SEQ ID No.: 4; wherein the one or more polypeptides are fused to an indicator reagent, an amino acid spacer, an amino acid linker, a signal sequence, a stop transfer sequence, a transmembrane domain, a protein purification ligand or a combination thereof.

20. The method of claim 19, wherein at least one of the polypeptides is in multimeric form.

21. The method of claim 11, wherein the test sample comprises a biological sample obtained from a mammal.

22. The method of claim 21, wherein the mammal is selected from the group consisting of humans, cats, horses, and dogs.

23. The method of claim 11, wherein the method comprises an assay selected from the group of assays consisting of a microtiter plate assay, reversible flow chromatographic binding assay, an enzyme linked immunosorbent assay, a radioimmunoassay, a hemagglutination assay a western blot assay, a fluorescence polarization immunoassay, and an indirect immunofluorescence assay.

24. The method of claim 11, wherein the polypeptide/antibody complexes are detected using a labeled anti-species antibody.

25. A method of detecting an *Ehrlichia ewingii* infection in a mammal comprising:
   (a) obtaining a biological sample from a mammal suspected of having an *E. ewingii* infection;
   (b) contacting a purified polypeptide consisting of SEQ ID No.: 1, SEQ ID No.: 2, SEQ ID No.: 3, SEQ ID No.: 4 or a combination thereof with the biological sample under conditions that allow polypeptide/antibody complexes to form;
   (c) detecting polypeptide/antibody complexes;
   wherein the detection of polypeptide/antibody complexes is an indication that the mammal has an *E. ewingii* infection and wherein the absence of polypeptide/antibody complexes is an indication that the mammal does not have an *E. ewingii* infection.

26. The method of claim 25, further comprising contacting the polypeptide/antibody complexes of (b) with an indicator reagent that generates a measurable signal prior to the performance of (c).

27. The method of claim 25, wherein the mammal is selected from the group consisting of humans, cats, horses, and dogs.

28. The method of claim 25, wherein the purified polypeptide is a fusion protein comprising one or more polypeptides of SEQ ID No.: I, SEQ ID No.: 2, SEQ ID No.: 3, SEQ ID No.: 4 wherein the one or more polypeptides are fused to an indicator reagent, an amino acid spacer, an amino acid linker, a signal sequence, a stop transfer sequence, a transmembrane domain, a protein purification ligand or a combination thereof.

* * * * *

SEQUENCE LISTING

<160> NUMBER OF SEQ ID NOS: 4

<210> SEQ ID NO 1
<211> LENGTH: 20
<212> TYPE: PRT
<213> ORGANISM: Ehrlichia ewingii -continued

```
<400> SEQUENCE: 1

Ala Glu Thr Lys Lys Thr Phe Gly Leu Glu Lys Asn Tyr Asp Gly Ala
1               5                   10                  15

Lys Ile Glu Asp
            20

<210> SEQ ID NO 2
<211> LENGTH: 20
<212> TYPE: PRT
<213> ORGANISM: Ehrlichia ewingii

<400> SEQUENCE: 2

Ala Glu Thr Lys Arg Thr Phe Gly Leu Asp Lys Asn Tyr Asp Gly Ala
1               5                   10                  15

Gln Ile Thr Asp
            20

<210> SEQ ID NO 3
<211> LENGTH: 20
<212> TYPE: PRT
<213> ORGANISM: Ehrlichia ewingii
<220> FEATURE:
<221> NAME/KEY: MISC_FEATURE
<222> LOCATION: (5)..(5)
<223> OTHER INFORMATION: X is any amino acid
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (17)..(17)
<223> OTHER INFORMATION: X is any amino acid
<220> FEATURE:
<221> NAME/KEY: MISC_FEATURE
<222> LOCATION: (19)..(19)
<223> OTHER INFORMATION: X is any amino acid

<400> SEQUENCE: 3

Ala Glu Thr Lys Xaa Thr Phe Gly Leu Xaa Lys Asn Tyr Asp Gly Ala
1               5                   10                  15

Xaa Ile Xaa Asp
            20

<210> SEQ ID NO 4
<211> LENGTH: 21
<212> TYPE: PRT
<213> ORGANISM: Ehrlichia ewingii
<220> FEATURE:
<221> NAME/KEY: MISC_FEATURE
<222> LOCATION: (1)..(1)
<223> OTHER INFORMATION: X is any amino acid
<220> FEATURE:
<221> NAME/KEY: MISC_FEATURE
<222> LOCATION: (6)..(6)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (18)..(18)
<223> OTHER INFORMATION: X is any amino acid
<220> FEATURE:
<221> NAME/KEY: MISC_FEATURE
<222> LOCATION: (20)..(20)
<223> OTHER INFORMATION: X is any amino acid
```

-continued

```
<400> SEQUENCE: 4

Xaa Ala Glu Thr Lys Xaa Thr Phe Gly Leu Xaa Lys Asn Tyr Asp Gly
1               5                   10                  15

Ala Xaa Ile Xaa Asp
            20
```